(12) United States Patent
Wolowelsky et al.

(10) Patent No.: US 8,462,983 B2
(45) Date of Patent: Jun. 11, 2013

(54) METHOD AND APPARATUS FOR GAS DETECTION BASED ON SPECTRAL SPATIAL MISREGISTRATION

(75) Inventors: Karni Wolowelsky, Misgav (IL); Zvi Figov, Beit Shemesh (IL)

(73) Assignee: Rafael Advanced Defense Systems Ltd, Haifa (IL)

( * ) Notice: Subject to any disclaimer, the term of this patent is extended or adjusted under 35 U.S.C. 154(b) by 489 days.

(21) Appl. No.: 12/937,266

(22) PCT Filed: Apr. 16, 2009

(86) PCT No.: PCT/IL2009/000416
§ 371 (c)(1),
(2), (4) Date: Oct. 10, 2010

(87) PCT Pub. No.: WO2009/125413
PCT Pub. Date: Oct. 15, 2009

(65) Prior Publication Data
US 2011/0044495 A1    Feb. 24, 2011

(30) Foreign Application Priority Data
Apr. 9, 2008 (IL) .......................... 190756

(51) Int. Cl.
*G06K 9/00* (2006.01)
*G06K 9/62* (2006.01)
*G06K 9/64* (2006.01)
*G06K 9/68* (2006.01)
*G01N 31/00* (2006.01)
*H01L 31/00* (2006.01)

(52) U.S. Cl.
USPC .......... 382/100; 382/181; 382/217; 250/330; 702/24

(58) Field of Classification Search
USPC .. 382/100, 181, 209, 217–223; 250/330–334; 702/24
See application file for complete search history.

(56) References Cited

U.S. PATENT DOCUMENTS

| | | | |
|---|---|---|---|
| 4,676,642 A |  | 6/1987 | French |
| 5,656,813 A | * | 8/1997 | Moore et al. ................. 250/330 |
| 6,297,504 B1 | * | 10/2001 | Andreou ...................... 250/330 |

(Continued)

OTHER PUBLICATIONS

Dell'Endice et al., "Scene-based method for spatial misregistration detection in hyperspectral imagery", Applied Optics 46, 2007, pp. 2803-2816.

(Continued)

*Primary Examiner* — Aaron W Carter
(74) *Attorney, Agent, or Firm* — Mark M Friedman

(57) ABSTRACT

In accordance with one embodiment, a method for remote identification of at least one gas includes sampling a plurality of spectral images of a scene wherein each spectral image is sampled at a different wavelength, providing a reference spectral image, and generating a spatial displacement expression by detecting the spatial misregistration in at least one region of the spectral images between the reference spectral image and at least one of the plurality of spectral images. At least one reference spatial displacement expression is provided corresponding to at least one gas, and at least one identification process is implemented to identify at least one gas. The identification process employs the generated spatial displacement expression and the at least one reference spatial displacement expression. Optionally the reference image is one of the sampled spectral images, the reference spatial displacement expression is provided from a general or adapted library, and the concentration of the gas can be determined.

20 Claims, 3 Drawing Sheets

U.S. PATENT DOCUMENTS

| | | | |
|---|---|---|---|
| 6,545,278 B1 | 4/2003 | Mottier et al. | |
| 6,665,438 B1 * | 12/2003 | Lin | 382/191 |
| 6,687,620 B1 * | 2/2004 | Haaland et al. | 702/22 |
| 6,750,453 B1 | 6/2004 | Nelson et al. | |
| 7,189,970 B2 * | 3/2007 | Racca et al. | 250/338.5 |
| 7,301,148 B2 | 11/2007 | Johnson | |
| 7,649,174 B2 * | 1/2010 | Mammen et al. | 250/330 |
| 7,796,833 B2 * | 9/2010 | Polonskiy et al. | 382/274 |
| 7,872,756 B2 * | 1/2011 | Oda | 356/456 |
| 7,910,890 B2 * | 3/2011 | Hinnrichs | 250/339.03 |
| 8,165,340 B2 * | 4/2012 | Conger et al. | 382/100 |
| 2009/0200466 A1 * | 8/2009 | Mammen et al. | 250/330 |
| 2009/0257622 A1 * | 10/2009 | Wolowelsky et al. | 382/103 |
| 2009/0321645 A1 * | 12/2009 | Hinnrichs | 250/338.5 |
| 2010/0018289 A1 * | 1/2010 | Oda | 73/25.05 |
| 2010/0078561 A1 * | 4/2010 | Gorin | 250/338.5 |
| 2010/0284570 A1 * | 11/2010 | Grimberg | 382/103 |
| 2011/0044495 A1 * | 2/2011 | Wolowelsky et al. | 382/100 |

OTHER PUBLICATIONS

Figov et al., "Co-registration of hyperspectral bands", Proceedings of SPIE—The International Society for Optical Engineering—Image and Signal Processing for Remote Sensing XII 2007 SPIE US, vol. 6748.

ZVI Figov et al "Co-Registration of Hyperspectral Bands" Proceedings of SPIE—The International Society for Optical Engineering—Image and Signal Processing for remote sensing X111 2007 SPIE US, vol. 6748, 2007, 67480S-1-67480S-12.

Figov Z et al:"Co-registration of hyperspectral bands" proceedings of spie—the international society for optical engineering—image and signal processing for remote sensing xIII 2007 spie US. vol. 6748, 2007, the whole document.

Dell'Endice F et al: "Scence-Basd Method for Spatital Misregistration Detection in Hyperspectral Imagery" Applied Optics , OSA, Optical Society of America, Washington, DC, vol. 46, No. 15, May 20, 2007, pp. 2803-2816.

* cited by examiner

METHOD AND APPARATUS FOR GAS DETECTION BASED ON SPECTRAL SPATIAL MISREGISTRATION

RELATED APPLICATIONS

This patent application is a U.S. National Phase Application of PCT/IL2009/000416 filed on Apr. 16, 2009, which claims priority of Israeli Patent Application No. 190756 filed Apr. 9, 2008, the contents of which are incorporated herein by reference.

FIELD OF THE INVENTION

The current invention relates to the field of spectral imaging, and in particular to the area of spectral processing for the detection of gases.

BACKGROUND OF THE INVENTION

There are many areas that require detection and identification of gases by remote sensing. Some examples include monitoring of pollution from ground stations by airborne sensors and by satellites, measuring trace gas constituents of the atmosphere, assessing the state of the environment, monitoring industrial effluents, detecting harmful gases, such as carbon monoxide, and anesthetic gases in the respiratory air of a patient.

U.S. Pat. No. 6,545,278 to Franois Mother and Scott Bruce for Gas Discriminating Gas Detector System and Method teaches an overview of gas detection systems based on measurement of absorption of electromagnetic radiation by a gas of interest. This patent teaches a gas detection system for detecting and measuring concentration of gases in a chamber containing an air/gas mix by providing an optical light source through the air/gas mixture to one or more light detectors and measuring the absorption by the air/gas mixture of light in the bands individually associated with the detection channels.

Electromagnetic radiation is subject to absorption and scattering by the atmosphere and surfaces on the path from the radiation source to a radiation sensor. An example in the atmosphere of the Earth is absorption by ozone, carbon dioxide and water. The gases in the atmosphere of the earth selectively impede the passing of electromagnetic radiation. Energy in certain wavelengths is allowed to pass through almost unchanged while other wavelengths are almost totally blocked.

A spectral band, or spectral region, is a well-defined, continuous wavelength range in the spectrum of reflected or radiated electromagnetic energy. A spectral image is an image of one spectral band of a scene taken with a sensor that is sensitive to electromagnetic energy in that spectral band. Each image is also referred to as a band. A multispectral image is an image which contains data from a plurality of spectral images. A well known multispectral (or multi-band image) is a RGB color image, consisting of a red, a green and a blue image, each of them taken with a sensor sensitive to a different band (wavelength). While the three band RGB example is well known, and is included in the definition of multispectral, in the field of the current invention, the term multispectral is conventionally used for data containing from tens to hundreds of bands. Another type of multispectral imaging is known as hyperspectral imaging (HSI). Hyperspectral data may contain hundreds to thousands of bands. Hyperspectral imaging can also be defined by the manner in which the data is collected. Hyperspectral data is a set of contiguous bands (usually by one sensor) whereas multispectral data is a set of optimally chosen spectral bands that are typically not contiguous and can be collected from multiple sensors.

U.S. Pat. No. 7,301,148 to Timothy J. Johnson for Method and System for Remote Detection of Gases teaches systems that use active sources of infrared (IR) radiation, such as Fourier Transform Infrared (FTIR) and teaches passive IR techniques. A system is provided that includes at least one extended source of broadband infrared radiation and a spectrally sensitive receiver positioned remotely from the source. The source and the receiver are oriented such that a surface of the source is in the field of view of the receiver. The source includes a heating component thermally coupled to the surface, and the heating component is configured to heat the surface to a temperature above ambient temperature. The receiver is operable to collect spectral infrared absorption data representative of a gas present between the source and the receiver.

U.S. Pat. No. 6,750,453 to Loren D. Nelson and Martin J. O'Brien for Methods of and apparatus for detecting low concentrations of target gases in the free atmosphere teaches an apparatus that includes a source that directs broadband modulated light into a region the free atmosphere in which target gas may be present. A gas correlation radiometer responds to light transmitted through the region. Separate radiometer channels respond to a single beam of light after transmission through the region. A beam splitter separates the beam into two beams, one directed into each of the channels. The two channels separately and simultaneously respond to a respective one of the light beams for separately and simultaneously generating signals that together indicate whether the target gas is in the free atmosphere.

U.S. Pat. No. 4,676,642 to Herbert A. French for Apparatus and method for remote sensing of gases, vapors, or aerosols teaches a remote sensor comprising a means to measure the change in temporal coherence of light of a selected narrow waveband when it interacts with the gas. The light can be provided by a laser source or filtered sun light.

Improvements to conventional methods of spectral imaging for gas detection are focused on avoiding, reducing, or compensating for optical effects that affect the accuracy of the spectral image. An example of this approach is described by Francesco Dell'Endice, ET. AL., in the paper "Scene-based method for spatial misregistration detection in hyperspectral imagery," Applied Optics 46, 2803-2816 (2007). The paper describes how hyperspectral imaging sensors suffer from spatial misregistration, an artifact that prevents the accurate acquisition of the spectra. The paper proposes a method for estimating spatial misregistration, identifying misalignments, and suggestions are given to correct for spatial misregistration.

Whereas conventional approaches in the art are focused on eliminating optical effects, which are considered a hindrance to attempts to provide gas identification, the current invention uses an optical effect of the spectral imaging process, namely, spectral misregistration, in an innovative method to provide detection and identification of gases by remote sensing.

SUMMARY

According to the teachings of the present embodiment there is provided a method for remote identification of at least one gas including: sampling a plurality of spectral images of a scene wherein each spectral image is sampled at a different wavelength; providing a reference spectral image; generating a spatial displacement expression by detecting the spatial misregistration in at least one region of the spectral images between the reference spectral image and at least one of the plurality of spectral images; providing at least one reference spatial displacement expression corresponding to at least one gas; and implementing at least one identification process to identify at least one gas, the identification process employing the generated spatial displacement expression and the at least one reference spatial displacement expression.

In an optional embodiment, the reference spectral image is one of the sampled spectral images. In another optional embodiment, the method further includes determining the concentration of the at least one gas. In another optional embodiment, the at least one reference spatial displacement expression is provided from a library of reference spatial displacement expressions. In another optional embodiment, the spectral images are of the entire the scene. In another optional embodiment, the spectral images are of an area of the scene. In another optional embodiment, the spectral images are of a pixel of the scene. In another optional embodiment, the library is a general-purpose library. In another optional embodiment, the library is adapted for the specific atmospheric conditions of the scene. In another optional embodiment, the library is adapted for the specific gas concentrations of the scene.

According to the teachings of the present embodiment there is provided a system for remote identification of at least one gas including: a spectral image sampling device configured to sample a plurality of spectral images of a scene wherein each spectral image is sampled at a different wavelength; a processing system including at least one processor, operationally connected to the spectral image sampling device, configured to: provide a reference spectral image; generate a spatial displacement expression by detecting the spatial misregistration in at least one region of the spectral images between the reference spectral image and at least one of the plurality of spectral images; provide at least one reference spatial displacement expression corresponding to at least one gas; and implement at least one identification process to identify at least one gas, the identification process employing the generated spatial displacement expression and the at least one reference spatial displacement expression.

In an optional embodiment, the reference spectral image is one of the sampled spectral images. In another optional embodiment, the system is further configured to determine the concentration of the at least one gas. In another optional embodiment, the system is operationally connected to a library of reference spatial displacement expressions, the library of reference spatial displacement expressions providing the at least one reference spatial displacement expression. In another optional embodiment, the spectral images are of the entire the scene. In another optional embodiment, the spectral images are of an area of the scene. In another optional embodiment, the spectral images are of a pixel of the scene. In another optional embodiment, the system is operationally connected to a multispectral imaging device, the multispectral imaging device providing the spectral images. In another optional embodiment, the system is operationally connected to a hyperspectral imaging device, the hyperspectral imaging device providing the spectral images. In another optional embodiment, the library is a general-purpose library. In another optional embodiment, the library is adapted for the specific atmospheric conditions of the scene. In another optional embodiment, the library is adapted for the specific gas concentrations of the scene.

DETAILED DESCRIPTION

Figure 1:
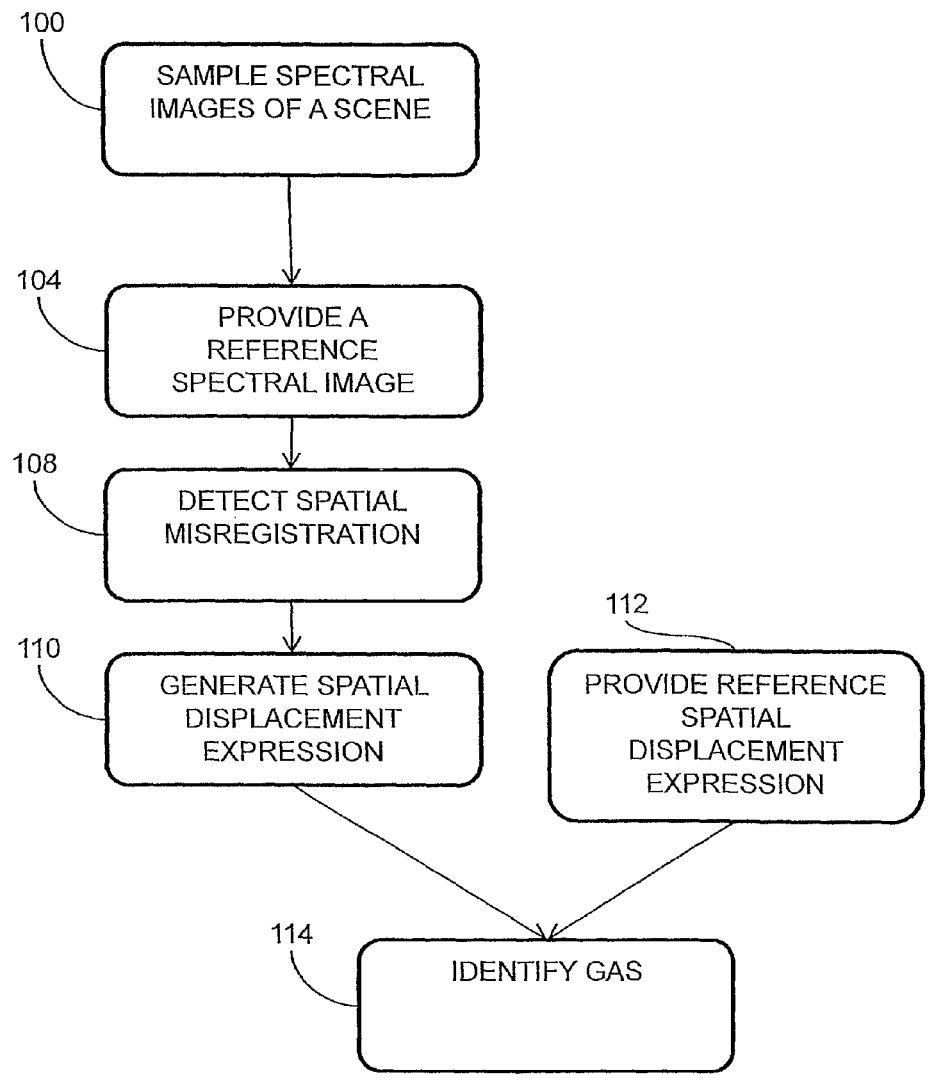
FIG. 1 is a flowchart of a method for gas detection based on spectral spatial misregistration.

The principles and operation for gas detection based on spectral spatial misregistration according to the present embodiment may be better understood with reference to the drawings and the accompanying description. A hyperspectral image consists of a great number of spectral images. Although these spectral images are obtained simultaneously, due to a number of optical effects the hyperspectral bands are not co-registered. Identification of the spatial misregistration can be done using an innovative method of subpixel image registration between spectral bands. This method generates a mapping of the gas absorption features that can be used for gas detection and identification.

In the context of this document, the wavelength is used to refer to a particular wavelength or a band of wavelengths around the particular wavelength value. The term gas includes any substance with relatively low density and viscosity with the ability to diffuse readily, as well as all gaseous elements, compounds or gas-borne droplets or particles.

Hyperspectral sensors collect information as a set of images. Each image represents a wavelength of the electromagnetic spectrum and is also known as a spectral band. This sequence of images can be combined to form a three dimensional hyperspectral cube as a way to handle the data for processing and analysis. The unprocessed (raw) spectral images can be combined to form a hyperspatial cube with or without various levels of processing. In one implementation, the unprocessed spectral images are processed to register them and then combined into a hyperspatial cube. In an alternative implementation having the same result, the unprocessed images that have been combined into a hyperspatial cube are processed to register the images and then re-combined into a new hyperspatial cube.

Image registration is the process of overlaying two or more images in correct alignment. Registration techniques are classified according to their nature and various techniques are known in the art, for example: area-based registration and feature-based registration. Each pixel in the hyperspectral cube is characterized by three indices $(x,y,\delta)$. Thus for each pixel $(x,y)$ in the spatial domain a complete spectrum allows us to obtain signatures characterizing the scene imaged. The accuracy of these signatures depends on many factors. One optical effect of hyperspectral collection is one spectral band ($\delta$) not corresponding spatially to another spectral band. This effect is known as spatial misregistration, and corresponds to the displacement which would be required to achieve registration between the corresponding regions of the images. In this description, the calculated spatial misregistration between a reference band and a spectral band is referred to as spatial displacement expression. There is a correlation between the spatial misregistration and atmospheric transmission. Spatial misregistration is particularly prominent in images of bands near the absorption bands of atmospheric gases.

Referring now to the drawings, FIG. 1 is a flowchart of a method for gas detection based on spectral spatial misregistration. Sampling spectral images of a scene is shown in block 100. Choosing one of the spectral images as a reference spectral image is shown in block 104. The spectral images are processed to detect spatial misregistration, shown in block 108. The spatial misregistration is used to generate a spatial displacement expression, shown in block 110. In block 112, a reference spatial displacement expression is provided. In block 114 at least one identification process uses the spatial displacement expressions to identify the gas.

Sampling spectral images of a scene is shown in block 100. The actual number of images can vary depending on the specific implementation of the method. At least two images are normally used, with hyperspectral imaging providing hundreds to thousands of images. A reference spectral image is provided, shown in block 104. In one implementation, the reference image is one of the sampled spectral images. Choosing the reference image can be done manually or directed by an automatic process. If one of the spectral images is of a band with no gas features present, it is preferable to use this spectral image as the reference image to provide improved processing. The other spectral images may contain at least one spectral band of at least one gas. In an optional implementation, the reference image can be a calculated mean position.

Figure 2:
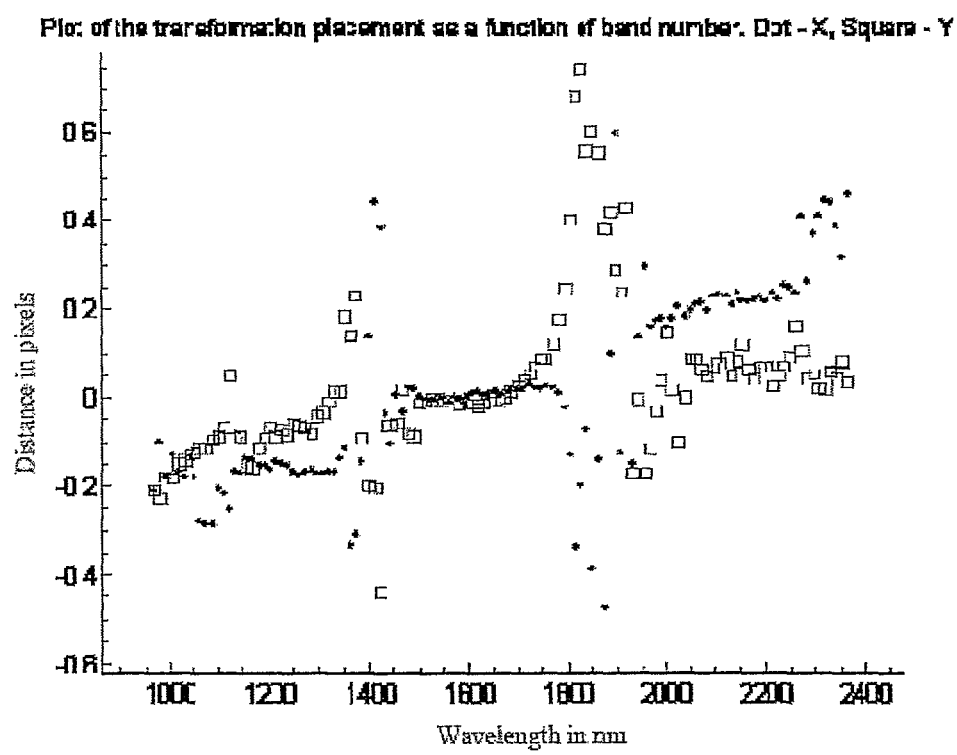
FIG. 2 is a plot of the x and y displacement for each spectral band.

The spectral images are processed in block 108 to detect spatial misregistration between the reference spectral image and the spectral images of the other bands. Note that processing of the spectral image is not limited to an entire scene. The spectral image can be the entire frame, a block (an area), or even a pixel from a scene. The process of detecting spatial misregistration finds the x,y spatial displacement, at a sub-pixel level, in a given spectral band (source) relative to a spectral reference band. This x,y spatial displacement (dx,dy) for each spectral band is the spatial misregistration. FIG. 2 is a plot of the x and y displacement for each spectral band using this method. The procedure is repeated twice, once to estimate dx and once to estimate dy. The first calculation is of all the subpixel displacements for all the rows of the source relative to the reference using the normalized correlation interpolated for subpixel accuracy. Next is obtaining an average row displacement using the average of all rows whose correlation coefficient is above a threshold. The same is done for the column disparity calculation after transforming and resampling the image using the average row displacement. Using an area-based registration technique facilitates a robust process using a "greedy" algorithm that tries to use as much of the image as possible and is less dependent on elements that may disappear in different areas of the spectrum.

The detected spatial misregistration from block 108 is used by block 110 to generate a spatial displacement expression. The spatial displacement expression is a set of numbers, or a corresponding function, that correspondingly correlates to the calculated spatial misregistration between a reference band and a spectral band. Note that the spatial displacement expression is not limited to being generated at the same location or immediately prior to performance of the subsequent analysis of the displacement expression, and can also be provided from another source, previously calculated and provided to the process, or generated by another means.

Providing a reference spatial displacement expression is shown in block 112. In the case of known gases, the spatial displacement expression can be provided from a library or other reference source. The library may be a general-purpose library or may be adapted for the specific atmospheric conditions to which the method is being implemented. Adaptation of the gas properties for the specific atmospheric conditions and/or gas concentrations can be done using known techniques such as MODTRAN simulation software.

In block 114 matching techniques are preferably applied to compare each generated spatial displacement expression with reference spatial displacement expressions. The identification process tries to identify a best match gas or combination of gases that correspond to the generated spatial displacement expression for each area (frame, block, or pixel). This processing can be performed by well-known techniques such as the Spectral Angle Mapper (SAM) classification or other techniques that are known in the art. A threshold is then typically applied for each gas to give an indication of what gases are present in that area (frame, block, or pixel).

The identification block 114 may optionally include other algorithms. In one optional implementation, block 114 detects the presence of gas. For detection of the presence of a gas, it may be sufficient to processes the generated spatial displacement expression, without the need to provide a reference spatial displacement expression for comparison. In this case, a technique such as threshold comparison can be used.

In another optional implementation, the identification block 114 may include an algorithm for determining the concentration of a gas. In certain applications, particularly in controlled environments where a specific target gas is to be detected, concentration derivation may be performed for a predetermined gas without a prior detection algorithm. Based on the classification output and/or the magnitude of the spatial movement, the path concentration can be estimated. In this case, the technique may or may not use a reference spatial displacement expression, or the technique may use other information to provide a concentration of the gas.

In one implementation, this method enables identification of a gas from a single frame without need for time analysis. This is particularly important when there is a slow dispersion, and can reduce false alarms. In another implementation, this method has been shown to work particularly well when the background is inhomogeneous. Conventional detection schemes either use the time analysis of the spectrum or assess the background when homogenous. The background is usually inhomogeneous in urban areas and airborne scenarios.

Figure 3:
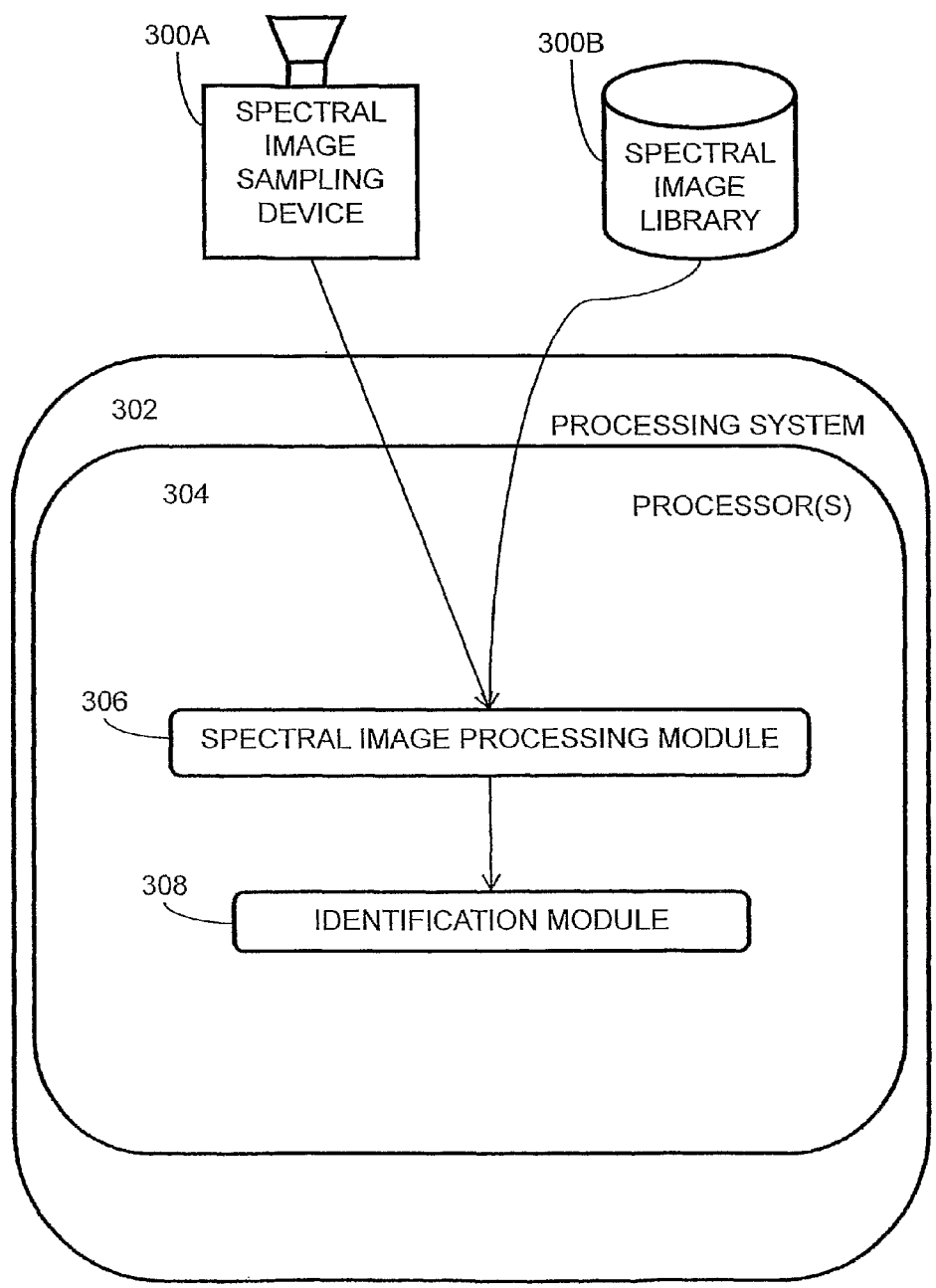
FIG. 3 is a diagram of a system for gas detection based on spectral spatial misregistration.

Referring now to the drawings, FIG. 3 is a diagram of a system for gas detection based on spectral spatial misregistration. A spectral image sampling device 300A or optionally a library of spectral images 300B are operationally connected to a processing system 302 containing one or more processors 304 configured for spectral image processing 306 and identification 308.

The spectral image-sampling device 300A is configured to sample a plurality of spectral images of a scene wherein each spectral image is sampled at a different wavelength. The actual number of spectral images sampled can vary depending on the specific implementation of the system. In one implementation, a multispectral imaging device samples a few to tens to a hundred spectral images of a scene. In another implementation, a hyperspectral image capture device can supply between hundreds and thousands of images for processing.

In an optional implementation, the spectral images can be provided from a library of spectral images 300B. In another optional implementation, the spectral images can be provided from one source or more than one source. If the spectral images are provided from different sources, the spectral images may require pre-processing or additional processing to compensate for differences between the sources and/or to achieve overall registration of the images to allow subsequent detection of localized misregistration. One example is that a different reference may be needed for different spectral ranges if the sensor contains separate imaging devices. In such cases, a translation transformation is typically not a sufficient mapping between devices. Other possible sources for providing spectral image will be obvious to one skilled in the art.

The spectral images are provided to a processing system 302 containing one or more processors 304. The processors are configured to process the spectral images 306. Processing includes choosing one of the spectral images as a reference image, then generating a spatial displacement expression by detecting the spatial misregistration in at least one region of the spectral images between said reference spectral image and at least one of said plurality of spectral images.

The generated spatial displacement expression is provided to an identification module 308. At least one reference spatial displacement expression is also provided to the identification module. This reference spatial displacement expression can be provided from a library or other sources as will be obvious to one skilled in the art. The library may be a general-purpose library, or adapted for the specific atmospheric conditions for which the system is used. The library can also be adapted for the specific gas concentrations for which the system is being used. The identification module implements at least one identification process to identify at least one gas, the identification process using the generated spatial displacement expression with at least one reference spatial displacement expression. In an optional implementation, the processors may additionally or alternatively be configured with an algorithm for determining the concentration of a gas. Note that the provided spectral images and the provided reference spatial displacement expressions can be of an entire scene, such as a frame, part of an image, known as a block, or a pixel.

It will be appreciated that the above descriptions are intended only to serve as examples, and that many other embodiments are possible within the scope of the present invention as defined in the appended claims.

What is claimed is:

1. A method for remote identification of at least one gas comprising:
    (a) sampling (100) a plurality of spectral images of a scene wherein each spectral image is sampled at a different wavelength;
    (b) providing (104) a reference spectral image;
    (c) generating (110) a spatial displacement expression by detecting the spatial misregistration in at least one region of the spectral images between said reference spectral image and at least one of said plurality of spectral images;
    (d) providing (112) at least one reference spatial displacement expression corresponding to at least one gas; and
    (e) implementing at least one identification process to identify (114) at least one gas, said identification process employing said generated spatial displacement expression and said at least one reference spatial displacement expression.

2. The method of claim 1 wherein said reference spectral image is one of said sampled spectral images.

3. The method of claim 1 further comprising determining the concentration of said at least one gas.

4. The method of claim 1 wherein said at least one reference spatial displacement expression is provided from a library of reference spatial displacement expressions.

5. The method of claim 4 wherein said library is a general-purpose library.

6. The method of claim 4 wherein said library is adapted for the specific atmospheric conditions of said scene.

7. The method of claim 4 wherein said library is adapted for the specific gas concentrations of said scene.

8. The method of claim 1 wherein said spectral images are of the entire said scene.

9. The method of claim 1 wherein said spectral images are of an area of said scene.

10. The method of claim 1 wherein said spectral images are of a pixel of said scene.

11. A system for remote identification of at least one gas comprising:
    (a) a spectral image sampling device (300A) configured to sample a plurality of spectral images of a scene wherein each spectral image is sampled at a different wavelength;
    (b) a processing system (302) including at least one processor (304), operationally connected to said spectral image sampling device (300A), configured to:
        (i) provide a reference spectral image;
        (ii) generate (306) a spatial displacement expression by detecting the spatial misregistration in at least one region of the spectral images between said reference spectral image and at least one of said plurality of spectral images;
        (iii) provide at least one reference spatial displacement expression corresponding to at least one gas; and
        (iv) implement at least one identification process (308) to identify at least one gas, said identification process employing said generated spatial displacement expression and said at least one reference spatial displacement expression.

12. The system of claim 11 wherein said reference spectral image is one of said sampled spectral images.

13. The system of claim 11 further configured to determine the concentration of said at least one gas.

14. The system of claim 11 operationally connected to a library (300B) of reference spatial displacement expressions, said library of reference spatial displacement expressions providing said at least one reference spatial displacement expression.

15. The system of claim 14 wherein said library (300B) is a general-purpose library.

16. The system of claim 11 wherein said spectral images are of the entire said scene.

17. The system of claim 11 wherein said spectral images are of an area of said scene.

18. The system of claim 11 wherein said spectral images are of a pixel of said scene.

19. The system of claim 11 operationally connected to a multispectral imaging device, said multispectral imaging device providing said spectral images.

20. The system of claim 11 operationally connected to a hyperspectral imaging device, said hyperspectral imaging device providing said spectral images.

* * * * *